United States Patent [19]

Schiff

[11] Patent Number: 4,697,573
[45] Date of Patent: * Oct. 6, 1987

[54] PERCUTANEOUS INTRA-AORTIC BALLOON AND METHOD FOR USING SAME

[75] Inventor: Peter Schiff, Cookeville, Tenn.

[73] Assignee: IABP Corporation, Boston, Mass.

[*] Notice: The portion of the term of this patent subsequent to Mar. 18, 2003 has been disclaimed.

[21] Appl. No.: 723,087

[22] Filed: Apr. 15, 1985

Related U.S. Application Data

[63] Continuation-in-part of Ser. No. 442,958, Nov. 19, 1982, Pat. No. 4,576,142.

[51] Int. Cl.⁴ .............................................. A61B 19/00
[52] U.S. Cl. .................................... 128/1 D; 604/264
[58] Field of Search ............... 128/1 D, 344, 769, 785; 604/96, 99, 103, 177, 264

[56] References Cited

U.S. PATENT DOCUMENTS

| | | | |
|---|---|---|---|
| 3,294,225 | 12/1966 | Kenyon | 206/446 |
| 3,595,230 | 7/1971 | Suzeoka | 604/171 |
| 4,276,874 | 7/1981 | Wolvek et al. | 604/96 |
| 4,362,150 | 12/1982 | Lombardi, Jr. et al. | 604/99 |
| 4,444,186 | 4/1984 | Wolvek et al. | 128/1 D |
| 4,576,142 | 3/1986 | Schiff | 128/1 D |

*Primary Examiner*—William E. Kamm

[57] ABSTRACT

An intra-aortic balloon assembly has a balloon whose distal end terminates in a tip and whose proximal end is joined to and communicates with the interior of a catheter tube. A slender stylet extends rearwardly from the tip through the balloon and catheter tube. The balloon is arranged so that its longitudinal axis is significantly displaced from the stylet facilitating tight wrapping of the balloon about the stylet in a single spiral in the same fashion that a flag is wrapped (i.e. "wound") about its supporting flag pole. The stylet may be affixed to the balloon and/or the catheter tube. The balloon is preferably pre-wrapped and is shipped to the user in the pre-wrapped condition. The balloon is retained in the wrapped condition by a removable holder having releasably joined holder halves encircling the wrapped balloon. The catheter tube is coupled to a sheath splitter and a luer connector having a slidably mounted control member for extending the balloon to prevent the wrapped balloon from lateral folding during inspection. The sheath splitter splits the insertion sheath after proper placement of the balloon by pulling the insertion sheath against the cutting edges of the sheath splitter.

39 Claims, 16 Drawing Figures

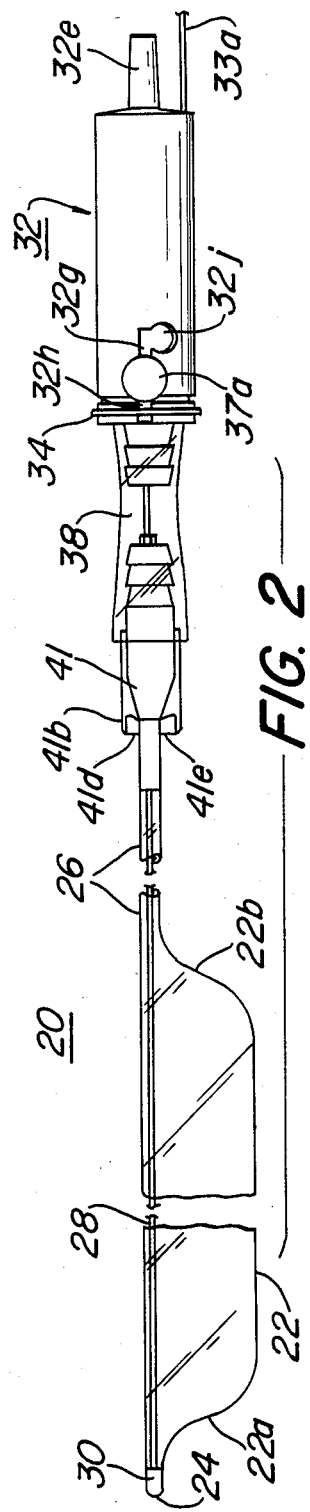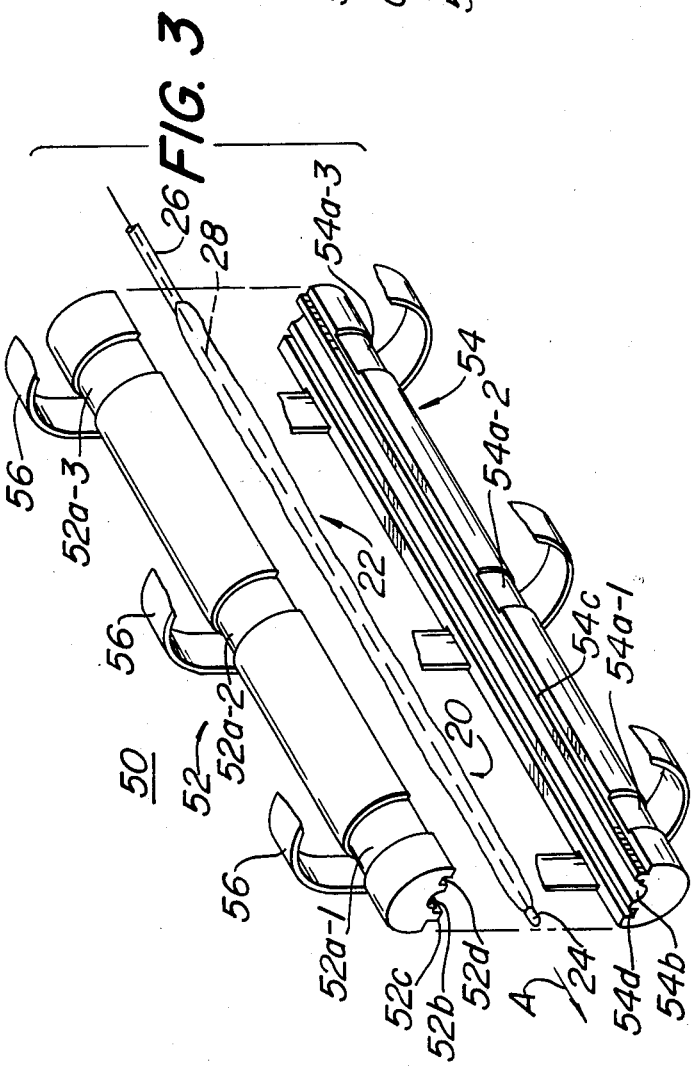

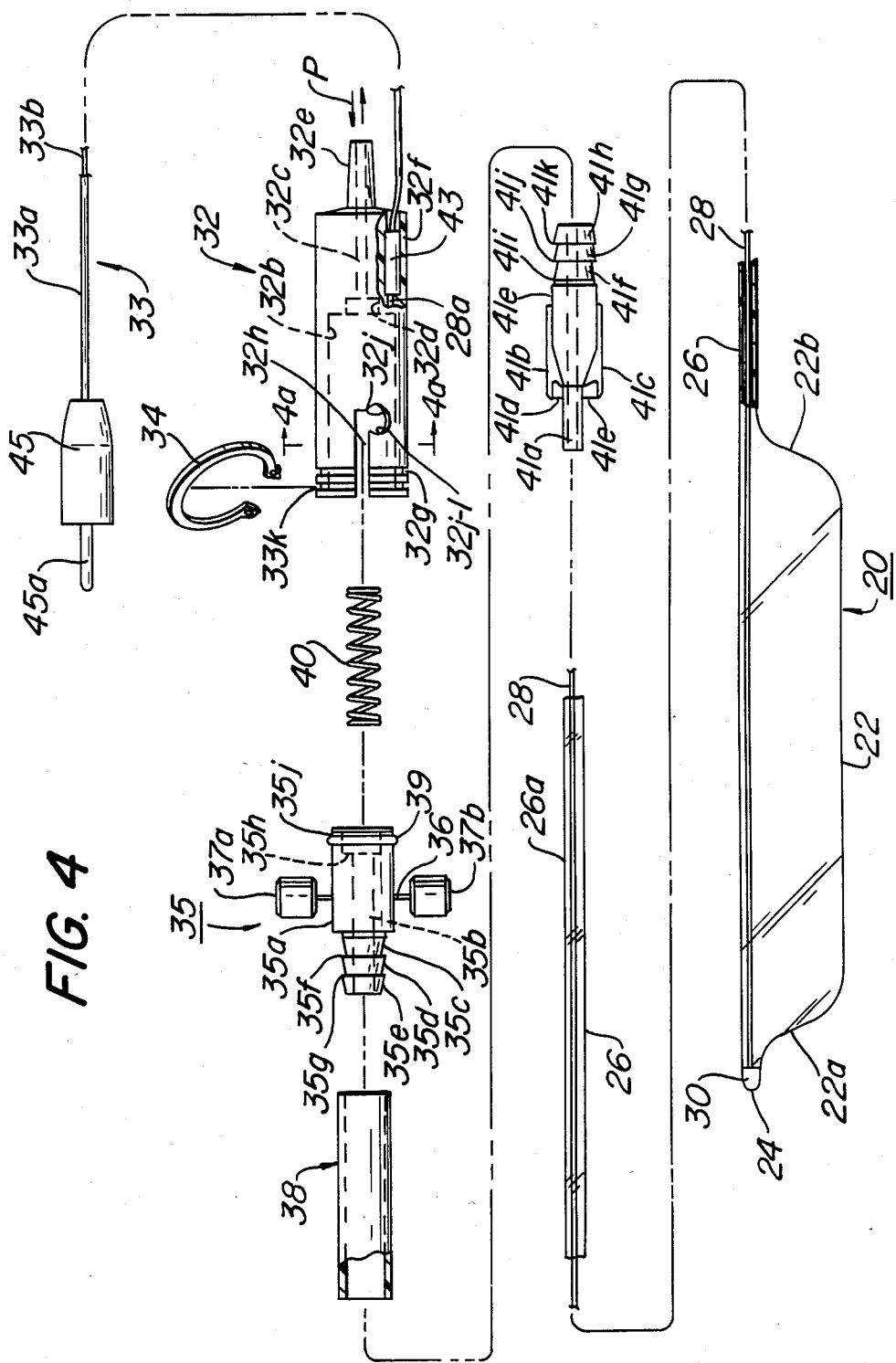

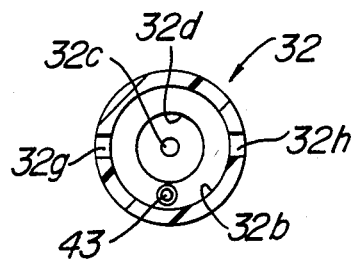
FIG. 4a
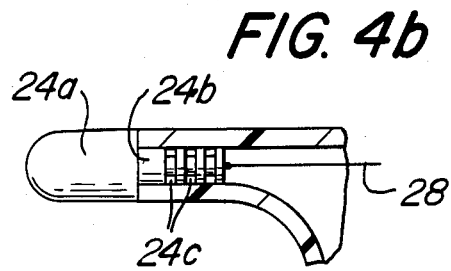
FIG. 4b
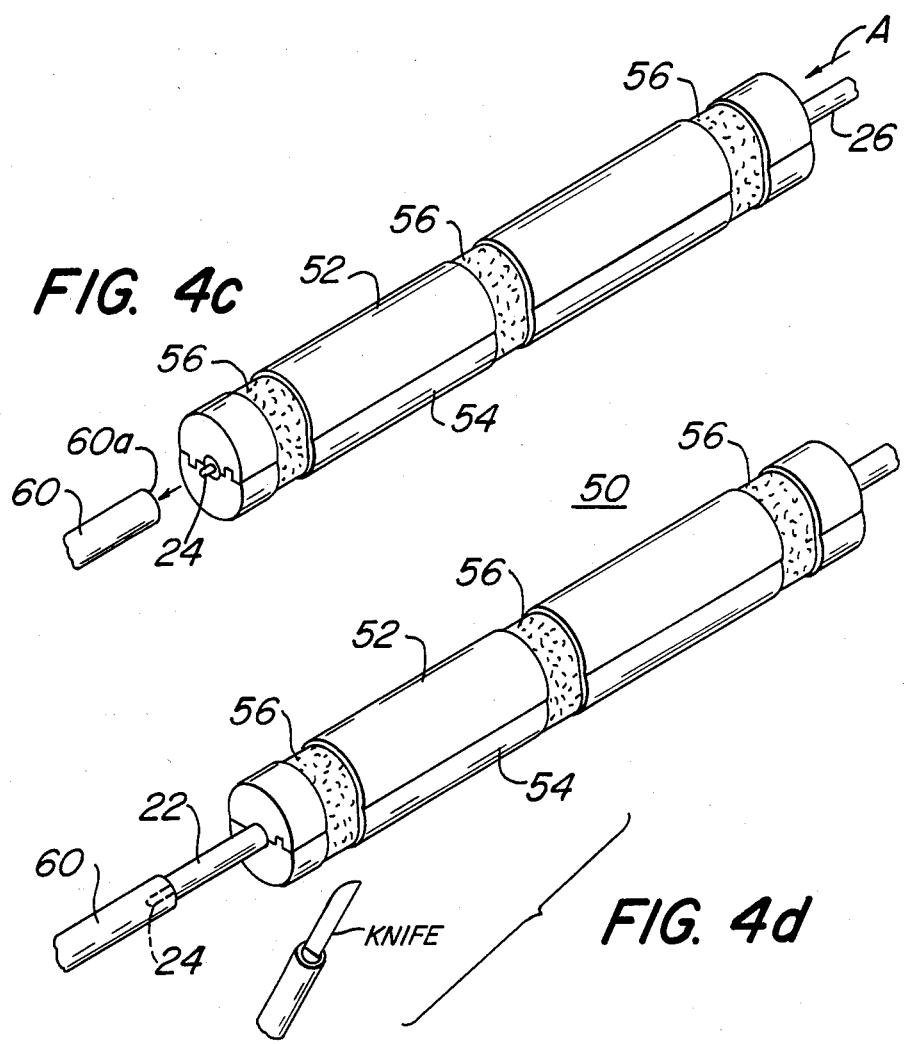
FIG. 4c
FIG. 4d

PERCUTANEOUS INTRA-AORTIC BALLOON AND METHOD FOR USING SAME

This application is a continuation-in-part of U.S. Ser. No. 442,958, filed Nov. 19, 1982, and issued Mar. 18, 1986, as U.S. Pat. No. 4,576,142.

FIELD OF THE INVENTION

The present invention relates to intra-aortic balloon assemblies and more particularly to method and apparatus for tightly wrapping the balloons of said assemblies and for holding and manipulating the wrapped balloon preparatory to insertion and particularly insertion employing a percutaneous technique.

BACKGROUND OF THE INVENTION

The use of intra-aortic balloon (IAB) assemblies for assisting the pumping action of the heart are well-known. Recently, research efforts have placed emphasis upon facilitating the insertion and placement of such balloon assemblies. One of the major objectives is to obtain reductions in balloon profile, i.e. outer diameter, in order to achieve the aforementioned results. Early efforts to achieve such results led to the technique of evacuating the balloon and wrapping the evacuated balloon about an elongated member substantially coaxial with the longitudinal axis of the balloon. This technique is disclosed in U.S. Pat. No. 3,939,820 issued on Feb. 24, 1976 to Grayzel, et al. Another technique comprised the evacuation of an IAB identified as the "PHASIC" balloon designed by the present inventor and inserted into a cannula grafted to a patient which balloon folded over itself upon insertion. Another technique adopted to achieve substantially similar results utilizes a twistable, elongated stylet coaxial with the longitudinal axis of the balloon, one end of the balloon being rotatable relative to the opposing end, and being twisted about the stylus in order to reduce the balloon profile. This technique is disclosed in U.S. Pat. No. 4,261,339 issued Apr. 14, 1981 in the name of Hanson, et al. A novel improvement on this technique is disclosed in application Ser. No. 253,680, filed Apr. 13, 1981 in the name of the inventor of the present invention, and disclosing an intra-aortic balloon assembly having a stylet rotatable through a manually operable control knob arranged remote from the balloon, for wrapping the balloon.

The balloons of the above techniques which employ a flexible stylet may be introduced into the body through a percutaneous technique such as, for example, the Seldinger technique, wherein an introducer sheath is initially introduced into the body and the balloon is thereafter introduced into the body by insertion into and through said introducer sheath, which may then be either partially or totally removed after the balloon has been properly placed.

Still another technique for reducing the profile of the balloon but without either wrapping or twisting, is disclosed in U.S. Pat. No. 4,327,709 issued on May 4, 1982, the Hanson, et al., and describing a technique in which the balloon is evacuated. Hanson alleges that the balloon membrane forms a flat tape-like cross-section with the stylet lying along the central axis thereof. Hanson further alleges that the two halves of the balloon lying on either side of the stylus are folded over to form first and second longitudinal folds. The balloon is thereafter inserted into one end of the insertion sheath used in the performance of the Seldinger technique. This technique assumes that the balloon will fold in the alleged manner and that it form a sufficient number of longitudinal folds to enable its insertion into the insertion sheath.

Although all of the above-mentioned techniques tend to reduce the profile of the balloon, they nevertheless exhibit certain disadvantages. For example, the balloon assemblies which rely upon twisting techniques create a large number of folds to generate a non-uniform helical pattern which may damage the introducer sheath and/or the patient or the balloon itself, which is greatly stressed by such wrapping. The balloon assemblies adapted for folding and/or wrapping techniques also create a large number of folds, due to their geometry and thus all of the above techniques fall short of reaching a minimal outer profile and without introducing additional disadvantages. In addition thereto, none of the above techniques teach a pre-wrapped balloon, or a method or means for maintaining a pre-wrapped balloon in the fully and tightly wrapped state, until it is ready for insertion and without stressing the membrane.

In an effort to overcome the disadvantages of the above-mentioned prior art, the inventor of the present invention has developed an intra-aortic balloon adapted for percutaneous insertion and a method for insertion of same which apparatus and method is set forth in copending application Ser. No. 442,958 filed Nov. 19, 1982. The intra-aortic balloon assembly described in the aforementioned copending application comprises a balloon having its distal end terminating in a tip and having its proximal end joined and communicating with the distal end of an elongated catheter tube. A flexible, slender stylet extends rearwardly from the tip of the balloon and into the catheter tube. The ends of the balloon respectively joining the tip and catheter tube are each displaced from the longitudinal axis of the balloon to position the stylet along an imaginary line which is displaced a substantial distance from the longitudinal axis of the balloon, when inflated, so that the stylet preferably rests against or is in close proximity to the interior surface of the balloon along the entire length thereof. The adjusted position of the balloon axis relative to the stylet enables the balloon to be wrapped more tightly and more easily than any of the conventional designs.

Wrapping is accomplished by evacuating the balloon so that it forms a flat, tape-like cross section. However, contrary to conventional designs, the stylet rests against the interior surface of one of the folds of the flattened balloon, enabling the balloon to be wrapped about the stylet in a single, continuous, tight spiral, in much the same way that a flag is wrapped about a flagpole.

The intra-aortic balloon design of the above-mentioned copending application utilizes a stylet which extends through the offset balloon and catheter and extends into a luer which is coupled to a rotatable, manually operable control knob to permit twisting or rotation of the stylet to compensate for any undesired twisting which may result from the wrapping operation.

Once the offset balloon is tightly wrapped about the stylet, the balloon is maintained in the fully wrapped position by means of holder halves which are releasably joined to one another to encircle the wrapped balloon and thereby retain the balloon in the tightly wrapped condition. The interior surfaces of the holder halves are preferably either formed of or coated with a low friction surface which permits the balloon to be easily pushed out of the holder assembly and into the insertion sheath. The holder halves are joined to one another by plastic strips of tape which are wrapped about the holder halves and adhesively joined thereto, the tape strips being easily cut away when it is desired to remove the holder halves from the intra-aortic balloon assembly. The interfitting of the holder halves by tongue and groove joints permit the tape strips to be severed by a sharp instrument without any danger of accidently cutting the balloon.

During insertion, the balloon experiences lateral folding as it is pushed through the sheath during balloon insertion or as it is pulled from an artery during balloon removal. This may cause serious injury to the patient.

BRIEF DESCRIPTION OF THE INVENTION

The present invention is characterized by comprising an intra-aortic balloon assembly and method and apparatus for tightly wrapping the balloon of the aforesaid assembly to achieve a small profile not heretofore obtainable through conventional techniques and further including method and apparatus for retaining the balloon in the fully and tightly wrapped state until it is ready for insertion and for facilitating insertion and/or removal of the balloon by preventing the formation of lateral folds.

The intra-aortic balloon assembly of the present invention comprises a balloon having its distal end terminating in a tip and having its proximal end joined and communicating with the distal end of an elongated catheter tube. A flexible slender stylet extends rearwardly from said tip through said balloon, said catheter tube and into a luer. The ends of the balloon joining said tip and said catheter tube are each displaced from the longitudinal axis of said balloon. Said balloon ends position the stylet along an imaginary line which is displaced a substantial distance from the longitudinal axis of the balloon so that the stylet preferably rests against the interior surface of the balloon along the entire length thereof. The juxtaposition of the balloon axis relative to the stylet enables the balloon to be wrapped more tightly and more easily than any of the conventional designs.

The proximal ends of the catheter and stylet pass through a sheath stripper coupled to a reciprocating luer connector control member by means of a piece of flexible tubing. The stylet extends through the sheath stripper member, flexible tubing and luer connector control member and has its proximal end secured against movement within the luer connection. The connector control member is mounted to reciprocate within the luer connector. Spring means normally biases the connector control member toward the pumping position. The connector control member is provided with a pair of control handles secured to a pin extending through the connector control member and arranged along an imaginary diameter thereof. The luer connector is provided with a pair of axially aligned slots for slideably receiving and guiding opposite ends of the aforementioned pin. The slots each terminate in a circular shaped opening. By moving the operating handles of the connector control member against the force of said bias means so that the opposite ends of the pins are arranged in the circular openings and slightly rotating the control member, the control member is locked into the insertion/removal position.

Movement of the control member in the aforesaid manner, actually moves the catheter tube relative to the stylet, causing the balloon to be slightly elongated, creating longitudinal tension in the balloon and eliminating "lateral" folds in the balloon membrane as it is pushed through the sheath during balloon insertion or as it is pulled from an artery during balloon removal.

Once the balloon is inserted, slight rotation of the connection control member by manipulation of its operating handles enables the control member to be urged in the direction of the force imposed by the bias means to relieve the tension imposed upon the balloon and to enable regular, periodic balloon inflation and deflation.

The intra-aortic balloon is removed by returning the connector control member to the insertion/removal position. The balloon is withdrawn by a "back and forth" movement comprised of pulling the balloon approximately two inches and thereafter pushing the balloon approximately one-half inch in alternating fashion, eliminating the forming of lateral folds in the balloon membrane and minimizing trauma to the artery.

The sheath stripper serves to facilitate complete removal of the insertion sheath by pulling the insertion sheath back against the sheath stripper enabling the sheath stripper cutters to split the insertion sheath in half. The balloon catheter has nearly the same diameter as the percutaneous dilator, preventing the artery from having to "close down" on the catheter when the sheath is totally removed, thereby virtually eliminating any bleeding. The sheath removal results in a large diameter catheter which provides rapid and more beneficial balloon response with less overall arterial obstruction.

The reciprocating connector control member is provided with an O-ring which cooperates with the interior surface of the luer connector to provide a sliding, air tight seal to provide absolute integrity of the conduit between the balloon and the pumping system.

The balloon terminates in a unique electrode tip connected to a wire at the luer coupling to provide a substantially improved ECG amplitude and more reliable balloon triggering.

OBJECTS OF THE INVENTION AND BRIEF DESCRIPTION OF THE FIGURES

It is, therefore, one object of the present invention to provide an intra-aortic balloon design which facilitates insertion of the balloon portion which is wrapped in a tight, continuous spiral about a stylet. The "old art" of wrapping also acts to "eliminate" the outer, longer, peripheral circumference since the outer circumference of the wrapped balloon "uses up" this length. The larger longitudinal periphery is "no factor" in the new folding technique of this invention.

Still another object of the present invention is to provide an intra-aortic balloon assembly which utilizes a control member which extends the wrapped balloon to facilitate inertion of the wrapped balloon.

Still another object of the present invention is to provide an intra-aortic balloon assembly in which a stylet extends through the entire length of the balloon portion thereof and terminates in an electrode tip for providing a monitoring signal during pumping.

Still another object of the present invention is to provide a holder assembly for intra-aortic balloons which retains the balloon in a tight wrap preparatory to use and permits easy removal from the holder assembly merely by pushing the intra-aortic balloon assembly through the holder assembly.

Still another object of the present invention is to provide a novel method and apparatus for percutaneously inserting tightly wrapped intra-aortic balloons and the like.

Still another object of the present invention is to provide an intra-aortic balloon assembly in which the longitudinal axis of the balloon portion is offset from the longitudinal axis of the catheter tube joined to the balloon portion, and including a sheath splitter for splitting an insertion sheath to facilitate its removal after insertion of the balloon.

The above, as well as other objects of the present invention, will become apparent when reading the accompanying description in conjunction with the drawing, in which:

FIG. 2 is a plan view showing an intra-aortic balloon assembly embodying the principles of the present invention.

FIG. 3 shows an exploded perspective view of a holder assembly embodying the principles of the present invention.

FIG. 3a shows the holder assembly of FIG. 3 in the fully assembled state.

FIG. 4 is an exploded plan view showing each of the components comprising the balloon assembly of FIG. 2.

FIG. 4a is an end view of the luer connector of FIG. 4.

FIG. 4b is an enlarged view of the balloon tip of FIG. 2.

FIGS. 4c and 4d are developmental views of the manner in which the wrapped balloon is withdrawn from the holder assembly of FIG. 3.

DETAILED DESCRIPTION OF THE INVENTION AND THE PREFERRED EMBODIMENTS THEREOF

Figure 1:
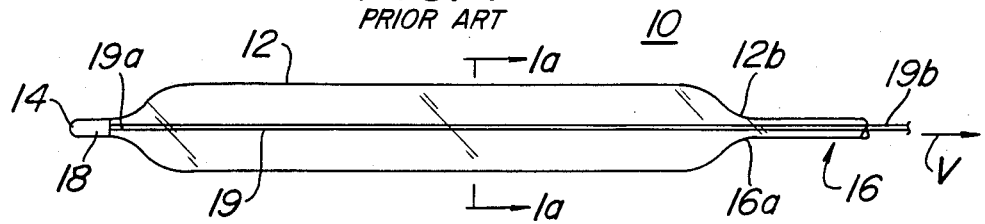
FIG. 1 shows a plan view of a prior art intra-aortic balloon.
Figure 1A:
FIG. 1a shows a cross-sectional view of the balloon assembly of FIG. 1 looking in the direction of arrows X—X and with the balloon in the quiescent state.
Figure 1B:
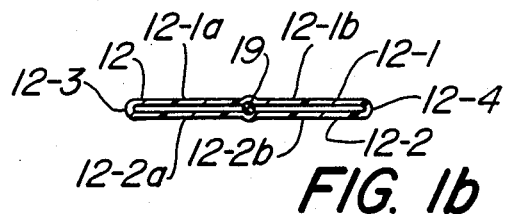
FIG. 1b is a sectional view looking in the direction of arrows X—X of FIG. 1 and with the balloon in the evacuated state.
Figure 1C:
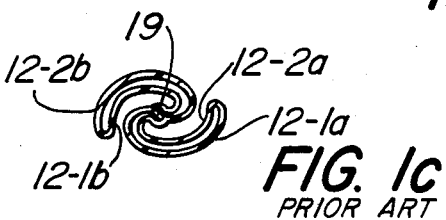
FIG. 1c is a cross-sectional view looking in the direction of arrows X—X of FIG. 1 and showing the manner in which the balloon may be wrapped.

FIGS. 1 through 1c show a prior art intra-aortic balloon assembly 10 comprised of a balloon portion 12 formed of a suitable plastic material which is flexible and bendable to permit the balloon to form an annular cross-section when inflated. However, the balloon material is substantially non-stretchable, so as to prevent balloon 12 from stretching during operation within a normal pressure range.

The distal end 12a of balloon 12 is tapered and terminates in a tip 14 which is preferably rounded to facilitate its insertion into the body and to prevent the balloon tip from damaging anything which it engages. The tip may be provided with a radiopaque member 18 which shows up well in fluoroscopes and/or X-rays and is useful in assuring proper placement of the balloon within the human body.

The balloon proximal end 12b is tapered in a similar fashion and merges with the distal end 16a of a hollow, flexible, elongated catheter tube, arranged to couple the balloon to a source (not shown) of selectively positive and negative pulsatile pressure respectively inflating and deflating the balloon in synchronism with the pumping of the heart. Although not shown for purposes of simplicity, it should be understood that catheter tube 16 is of a length sufficient to have its proximal end extend outside of the body when the balloon 12 is properly positioned.

The balloon assembly 10 further includes a slender, flexible, elongated stylet 19, whose distal end terminates in tip 14. Stylet 19 extends rearwardly from tip 14 through the entire balloon 12 and into catheter 16. The stylet serves as the means about which the balloon 12 is wrapped or twisted, depending upon which of these two techniques is employed.

FIG. 1a shows a cross-section of balloon 12, wherein it can be seen that stylet 19 is coaxial with the longitudinal axis of balloon 12 when in the quiescent state. In the latter state, the balloon assumes an annular cross-section which is not perfectly circular, but is nearly so, as shown in FIG. 1a.

When it is desired to insert the balloon assembly 10 in accordance with one of the above-mentioned prior art techniques, a vacuum V may or may not be drawn through catheter 16, evacuating balloon 12, causing the balloon 12 to assume the tape-like cross-section shown in FIG. 1b and which is defined by two substantially flat surface portions 12-1 and 12-2, integrally joined to one another along folds 12-3 and 12-4. As can be seen from FIG. 1, stylet 19 is coaxial with the longitudinal axis of balloon 12.

In accordance with one technique, the balloon in the configuration shown in FIG. 1b is folded to form folds respectively intermediate the left-hand fold 12-3 and stylet 19, and intermediate to right-hand fold 12-4 and stylet 19. The balloon, in this folded state, is then inserted into an insertion sheath which causes the balloon to form additional folds in order to facilitate its passage along the insertion sheath.

The balloon 12 may also be wrapped after evacuation. The balloon may first be evacuated to form the tape-like cross-section shown in FIG. 1b, the flat portions of the balloon extending to opposite sides of stylet 19 in a manner shown in FIG. 1c. Thereafter the two halves of the balloon 12 are spirally wrapped about centrally located stylet 19, as shown in FIG. 1c. This is preformed by twisting the proximal end 12b with respect to the distal end 19a. The disadvantage of this arrangement resides in the fact that two separate spirally wrapped halves of the balloon 12 are formed about stylet 19. Since the outer balloon portions, i.e. right-hand half 12-2b of balloon portion 12-2, and the left hand half 12-1a of balloon portion 12-1 (note also FIG. 1b) form the outside of these spirals, these balloon portions extend over a longer path than the "inside" balloon portions 12-1b and 12-2a, thereby contributing to a nonuniform spiral wrapping of balloon 12. Since the spiral is made up of four surface layers, the nonuniformity is greatly multiplied, resulting in the formation of many additional folds and thereby making it difficult to obtain a tight compact wrap, and further contributing to a nonuniform spiral wrapping.

FIG. 2 shows an intra-aortic balloon assembly 20 designed in accordance with the principles of the present invention and comprised of a balloon 22 tapering at 22a and air-tightly joined to a conductive, metallic tip 24 at its distal end. Its proximal end 22b is tapered as shown, and is joined to catheter tube 26. A stylet 28 has its distal end extending into tip 24. Stylet 28 extends rearwardly through balloon 22 into catheter tube 26 and coupling member 32 and has its proximal end 28a extending into and secured within a hollow tubular member 43 which, in turn, is secured within an elongated opening 32f in coupling 32. The bare end 33a of a wire covered with an insulating sleeve 33 extends into the right hand end of metallic tube 43 and is crimped to stylet 28 to provide good electrical contact, as shown in FIG. 4.

Stylet 28 extends partially through a central opening 32b in coupling 32 and extends into bore 32f. The central bore 32b extends rearwardly and communicates with opening 32c for coupling with means (not shown) for selectively providing positive and negative pulsatile pressure P for respectively inflating and deflating balloon 22, preferably in a predetermined relationship with the pumping of the patient's heart.

The distal end of stylet 28 is preferably mechanically secured and electrically connected to tip 24. Tip 24 may be metallic or may also be provided with a radio-pague member 30, visible on a fluorscope or in an X-ray for facilitating proper positioning of the intra-aortic balloon assembly 20. Tip 24 has rounded end 24a of larger diameter and a rear portion 24b of smaller diameter. The rear portion 24b is provided with annular grooves 24c to enhance the air-tight seal between the distal end of balloon 22 and tip portion 24b, as shown in FIG. 4b.

Although not shown for purposes of simplicity, it should be noted that catheter tube 26 has as a length sufficient to assure that coupling 32 is exterior to the body of the patient when balloon 22 is properly positioned.

Luer connector 32 is provided with an opening 32c (FIG. 4) communicating with central opening 32b and of a reduced diameter, forming a recess 32d therebetween. Opening 32c communicates with hollow projection 32e which is adapted to be coupled to a source of pulsatile negative and positive pressure means P (not shown for purposes of simplicity). Opening 32f extending substantially parallel to opening 32c and communicating the exterior of luer connector 32 with the hollow interior 32b is utilized for insertion of an insulated conductor 33 having an insulating sheath 33a covering wire 33b. Wire b is electrically coupled to stylet 28 within tube 43 for establishing an electrical path between conductive tip 24, stylet 28, conductor 33 and electrode 45a extending outwardly from rigid plastic member 45 for electrical connection into a monitor source for monitoring the heart in order to synchronize the pumping operation with the patient's heart.

Luer connector 32 is further provided with a pair of axially aligned slots 32g, 32h, note also FIG. 4a, which extend to the left-hand end of connector 32 and which terminate at their right-hand ends in an enlarged circular shaped opening 32j, only one of which is shown in FIG. 4. The periphery of luer connector 32 is further provided with a pair of annular grooves 32k. A resilient, metallic C-clip 34 is positioned in one of said grooves for retaining luer connector control member 35 within the luer connector 32.

Luer connector 35 is comprised of a cylindrical body portion 35a having a hollow bore 35b extending between the right and left-hand ends thereof. A pin 36 is aligned along an imaginary diameter of cylindrical body portion 35a and extends outwardly and beyond cylindrical body portion 35a. A pair of manually operable manipulating handles 37a, 37b are secured to the free ends of pin 36. The left-hand end of control member 35 is provided with a projection having a plurality of truncated conical sections 35c, 35d and 35e which form sharp vertices 35f and 35g for firmly biting into and gripping the interior surface of a short section of a flexible plastic tube 38.

Control member 35 is further provided with an annular groove 35j for receiving a resilient O-ring 39 which forms an air-tight sliding seal with the interior surface of bore 32b in luer connector 32.

A helical spring 40 is positioned within luer connector 32 and has its right-hand end seated within recess 32d and has its left-hand seated within recess 35h in cylindrical body portion 35a.

A sheath splitter 41 is comprised of a hollow metallic tubular section 41a whose central portion is provided with a pair of radially outwardly extending projections 41b, 41c, whose left-hand ends are provided with radially extended cutting edges 41d, 41e respectively. A plastic section 41e is molded about the right-hand portion of metallic portion 41a and extends to the right, forming three truncated, conical sections 41f, 41g and 41h which define sharp vertices 41i, 41j and 41k respectively for firmly biting into and gripping the interior surface of flexible plastic tubular section 38.

The distal end 26a of catheter tube 26 extends into the left-hand end of tubular section 41a and preferably extends at least partially into flexible tubular section 38. Stylet 28 extends through the hollow interior of sheath splitter 41, flexible tubular section 38 and control member 35 and terminates in luer connector 32, being coupled to tube 43 which is secured within bore 32f.

Control member 35 is slidably mounted within the bore 32b of luer connector 32 and is moveable to the left relative to FIGS. 2 and 4 with its movement in the left-hand direction being limited engagement of pin 36 by C-clip 34. Control member 35 is also moveable to the right being limited in the right-hand movement by the end of circular openings 32j. As can be seen from FIG. 4, the offset portion 32j-l of circular opening 32j enables pin 36 to be positioned offset from the axially aligned guide slot 32h and to be locked in this position. Control member is moved by urging handles 37a, 37b toward the right until pin 36 moves into circular opening 32j. Thereafter, the manual control handles 37a, 37b are manipulated to slightly rotate control member 35 so that each pin portion enters the associated offset portion for example, shown in FIG. 4. The portion of the pin moved into circular opening 32j is positioned in offset portion 32j-l where it is locked against any movement to the left when released, spring 40 urging control member 35 and hence pin 36 against the offset portion 32j-l and retaining it in this position.

The control member 35 may be moved out of the locked or pumping position simply by slightly rotating the control member 35 through manipulation of control knobs 37a, 37b to align pin 36 with the guide slots 32g, 32h whereupon spring 40 will urge control member 35 to the left, relative to FIG. 4.

Since the proximal end of stylet 28 is fixed within luer connector 32, movement of control member 35 to the right relative to FIG. 4 mover tube 38, splitter 41 and tube 26 to the right causing the wrapped balloon 22 to be stretched by an amount sufficient to prevent the wrapped balloon from being laterally folded during insertion, as will be more fully described.

Figure 2A:
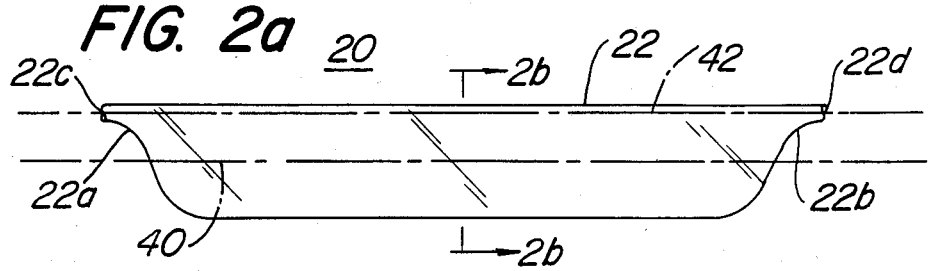
FIG. 2a shows a perspective view of the balloon portion of FIG. 2.

FIG. 2a shows in enlarged perspective view of balloon 22. The intermediate portion of balloon 22 defines a substantially annular cross-section when in the quiescent state, as shown in FIG. 2a. The intermediate portion is substantially concentric about a longitudinal axis represented by phantom line 40. The tapered portions 22a and 22b are generally in the form of non-concentric cones of revolution which cause the openings 22c and 22d to be offset from longitudinal axis 40 and to have their centers lie along phantom line 42, which passes through the centers of openings 22c and 22d and can clearly be seen to be substantially offset (i.e. displaced) from phantom line 40. As can clearly be seen from FIG. 2, stylet 28 passes through openings 22c and 22d and thereby is coaxial with imaginary line 42 and is similarly significantly displaced from imaginary line 40.

Figure 2B:
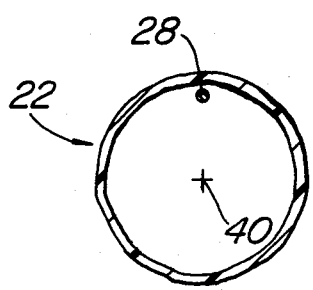
FIG. 2b is a sectional view of the balloon portion of FIG. 2a looking in the direction of arrows Y—Y and showing the balloon portion in the quiescent state.

FIG. 2b shows a cross-sectional view of the intermediate portion of balloon 22 where it can be seen that stylet 28 lies in close proximity to the interior surface of balloon 22.

Figure 2C:
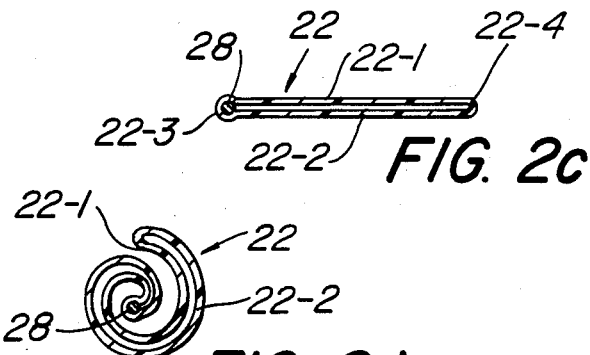
FIG. 2c is a sectional view looking in the direction of arrows Y—Y of FIG. 2a and showing the balloon in the evacuated state.
Figure 2D:
FIG. 2d is a sectional view looking in the direction of arrows Y—Y of FIG. 2a and showing the manner in which the evacuated balloon is wrapped.

FIG. 2c shows the balloon 22 after having been evacuated by drawing a vacuum through coupling 32. It can be seen that the balloon forms a tape-like cross-section similar to that formed by balloon 12 as shown in FIG. 1b, in which surface portions 22-1 and 22-2 are substantially flat and are integrally joined to one another along folds 22-3 and 22-4. Stylet 28 is positioned within the interior of fold 22-3, as shown.

Balloon assembly 20, shown in FIGS. 2-2c, may be wrapped in a tight spiral in the following manner:

The balloon is evacuated by drawings a vacuum through coupling 32 to form the cross-sectional configuration shown in FIG. 2c. While maintaining the vacuum condition, the balloon 22 is wrapped in a single spiral about stylet 28. Since the inside portion 22-1 in FIG. 2d must be slightly shorter than the outside portion 22-2, it may be necessary to periodically relieve and re-apply the vacuum the allow sections 22-1 and 22-2 to slide freely with respect to one another during wrapping. The arrangement of stylet 28 within the interior of one fold of the flat balloon forms only a single tape-like portion which is wrapped about stylet 28 in the manner shown in FIG. 2d. Thus, the balloon 22 is wrapped in only a single spiral about stylet 28 as shown in FIG. 2c reducing the total number of layers wrapped about stylet 28 from 4 to 2, and further reducing the inside and outside differential distances wrapped about the stylet 28 from 4 to 2. Since the balloon membrane lies flat to begin with and the balloon membrane is wound up "like a flag abouts its flagpole", no additional folds are created during winding of the balloon as compared with balloons in which one end is twisted relative to the other, thus lending itself to the formation of a much more uniformly wrapped balloon which wrap forms a tighter spiral than is capable of being obtained from the balloon configuration shown in FIGS. 1 through 1c. In addition, only one tape-like portion need be manipulated during the wrapping operation of the balloon 22, whereas two separate tape-like portions must be manipulated when wrapping balloon 12, as shown best in FIG. 1c.

The stylet 28 may be free of the interior surface of balloon 22, or alternatively may be secured to the interior surface by suitable means such as by cementing or bonding the same thereto. This may be accomplished, for example, in the manner described in detail in co-pending application Ser. No. 442,958 filed Nov. 19, 1982.

Once the balloon 12 is wrapped, suitable means must be provided for maintaining the balloon 22 in the tightly wrapped condition. Although retaining the balloon in the evacuated state retains the balloon in the flat, tape-like configuration, the vacuum condition will not hold the balloon in a tight spiral. A novel and unique arrangement for retaining the balloon in the tightly wrapped condition is embodied in the holder assembly 50 shown in FIGS. 3 and 3a which is comprised of a pair of elongated holder halves 52 and 54 having a substantially semi-circular cross-sectional configuration. The circular outer peripheries 52a and 54a are slightly greater than a half circle, as can best be seen in FIG. 3a, and are provided with shallow recesses 52a-1 through 52a-3, and 54a-1 through 54a-3.

The holder halves 52 and 54 are further provided with elongated semicircular-shaped grooves 52b and 54b and with an elongated projection 52c, 54c along one side of the elongated semicircular grooves 52b, 54b and with an elongated groove 52d, 54d on the opposite side of said semi-circular grooves 52b and 54b.

In use, projections (i.e. "tongues") 52c and 54c are arranged to fit into grooves 54d and 52d respectively, as shown best in FIG. 3a. When interfitted in this manner, the semi-circular-shaped grooves 52b and 54b cooperatively define an elongated hollow annular bore for receiving the wrapped balloon 22.

The holder assembly 50 is used in the following manner:

The balloon 22 is evacuated and wrapped in a tight spiral in the same manner as was previously described. The spirally wrapped balloon 22 is then set into the semi-circular groove 54b, for example, of holder half 54. The other holder half 52 is then interfitted with holder half 54 with the projections of each holder half being inserted into an associated groove of the other holder half, as was described hereinabove.

Holder halves 52 and 54 are retained in the assembled position shown in FIG. 3a by the provision of suitable tie means wrapped about the holder halves after assembly.

In the preferred embodiment shown in FIG. 3, the tie means comprises several plastic strips 56 each forming a closed loop and arranged within the recesses provided about holder halves 52 and 54. For example, it should be noted that recesses 52a-1 and 54a-1 are in alignment when the holder halves 52 and 54 are joined, as shown in FIG. 3a. The left-hand-most strip 56 is seated within these cooperating recesses. The plastic strip 56 is preferably of the heat-shrink type wherein the application of the heat causes the closed-loop strip 56 to shrink and thereby tightly encircle holder halves 52 and 54. The remaining strips are arranged within associated cooperating recessed pairs in a similar fashion. It should be understood that any other type of tie means may be provided such as, for example, a strip having a pressure-sensitive adhesive which may be wrapped around each recess one or more times. A soft plastic or metallic wire or cord may also be wrapped around each recess, the recesses being designed to accommodate and conform to such a wire.

A holder assembly 50, once fully assembled and retained in the assembled state, serves to retain the balloon 22 tightly wrapped until ready for use.

The holder halves 52, 54 are preferably formed of a plastic material having a very low coefficient of sliding friction. One suitable material is polytetrafluoroethylene. Alternatively, the holder halves may be formed of another material, which may be either plastic or metal and in which at least the surfaces of the elongated semi-circular grooves 52b and 54b are coated with a material providing a low coefficient of sliding friction. Alternatively, or in addition to the low friction surface, the semi-circular groove may be coated with a lubricant which is nontoxic and which has no harmful effect either to the balloon 22 or holder 50, or to the patent.

When it is desired to use the balloon assembly 20, for example, for percutaneous insertion into a patient, a sheath, not shown, is inserted into the body of the patient in accordance with the Seldinger technique, for example. The insertion sheath is shown in copending application Ser. No. 442,958 referred to hereinabove.

Once the sheath is properly inserted in the patient, the control member 35 is moved to the right, as was described herein above relative to FIG. 4, causing the balloon to undergo a predetermined amount of stretching. Thereafter, the balloon 22 is removed from the holder assembly 50 by gripping holder assembly 50 in one hand, gripping catheter tube 26 in the other hand, and moving catheter tube 26 in the direction shown by arrow A relative to holder assembly 50, (see FIG. 3), causing the wrapped balloon 22 to emerge from the left-hand end of holder 50. According to FIG. 4d, the tip 24 of the balloon assembly 20 is placed into the opening 60a in insertion sheath 60 before the balloon 22 is completely removed from holder assembly 50. Catheter tube 26 is moved relative to holder assembly 50, and into the insertion sheath whereupon the holder assembly may then be taken apart and discarded. To disassemble the holder assembly, plastic strips 56 may be served by a sharp knife or other instrument preferably positioned in the region of either joint, as shown by arrows B and C in FIG. 3a. Placing a sharp instrument in this position does not jeopardize the integrity of the balloon assembly 20, since the projections 52c and 54c (FIG. 3a prevent the knife or other sharp instrument from moving beyond the projection and engaging the balloon).

The plastic strips 56 are then discarded, and the holder halves 52 and 54 separated from one another and may also be discarded. This arrangement assures that the balloon 22 will be retained tightly wrapped until use, and in addition, provides a simple means for removing the balloon from the holder assembly in readiness for its insertion into a patient.

Once the balloon is properly positioned just below the aortic arch, the insertion sheath is removed from the patient by being pulled out of the body. The rearward end of the insertion sheath is pulled against the cutting edges 41d, 41e of the sheath splitter 41, shown in FIG. 2, causing the insertion sheath to be split in half. This is accomplished by pulling the insertion sheath backwardly against the sheath splitter 41 while holding the sheath splitter. The insertion sheath is fully removed from the body and, after having been completely split, is discarded.

Thereafter, the operating handle 37a, 37b of control member 35 are manipulated to move the pin 36 out of the offset position and into alignment with guide slots 32g, 32h, whereupon spring 40 urges control member 35 to the left relative to FIG. 4 thereby moving catheter tube 26 to the left relative to stylet 28 and relieving the balloon 22 of the stretching previously experienced by the balloon.

Projection 32e is coupled to a source of negative and positive pulsatile pressure and the pumping action causes the balloon 22 to become unfurled from the stylet 28. After weaning, the balloon is disconnected from the pumping system providing the positive and negative pulsatile sources. The luer connector control member 35 is then moved to the right relative to FIG. 1 to return pin 36 into the offset position to cause the balloon to be stretched a predetermined amount. The balloon is then withdrawn by a series of "back and forth" movements preferably including pulling the catheter tube 26 approximately two inches and thereafter pushing the catheter tube back into the body approximately one-half inch. These alternate "back and forth" movements are continued until the balloon is removed from the body. The movement of the balloon luer connector control member 35 into the aforementioned offset position for removing the balloon, together with the "back and forth" movements eliminate lateral folds from being formed in the balloon membrane and minimize trauma to the artery.

The positive and negative pulsatile pressure source is coupled to the balloon through projection 32e, bore 32c, bore 32b, central opening 35b in control member 35, flexible tubular section 38; and the hollow interior of sheath splitter 41 which communicates with catheter tube 26 to introduce negative and positive pressure pulses into balloon 22. Flexible resilient O-ring 39 forms an air-tight sliding seal with the interior surface of bore 32b in luer connector 32 to assure the integrity of the composite passageway between the pumping unit and the balloon 22.

Since the balloon catheter 26 is nearly the same diameter as the percutaneous dilator employed during the Seldinger technique for percutaneous insertion, the artery does not have to appreciably "close down" on the catheter tube when the insertion sheath is totally removed. Thus bleeding is virtually eliminated. This results in the provision of a catheter tube of large diameter providing rapid and more beneficial response with less overall arterial obstruction than smaller balloon catheters.

A latitude of modification, change and substitution is intended in the foregoing disclosure and in some instances some features of the invention will be employed without a corresponding use of other features. Accordingly, it is appropriate that the appended claims be construed broadly and in a manner consistent with the spirit and scope of the invention herein. For example, the balloon membrane 22 may be "wound like a flag" starting from the middle of the balloon member (FIG. 1b) after the balloon member is longitudinally extended. The balloon would then be wound in a symmetrical manner about the stylet (FIG. 1c). This wound balloon has the slight disadvantage of having two additional creases, compared to the wound balloon of FIG. 2d. However, the balloon of FIG. 1c will not have the many folds of a conventional twisted balloon.

What is claimed is:

1. A balloon assembly adapted for facilitating insertion in a vessel comprising:
   an elongated catheter tube;

an elongated balloon having a proximal end joined to one end of said catheter tube and having an opposite, distal end terminating in a tip;

a stylet having a distal end terminating in said tip and extending through said balloon and into said catheter tube;

said balloon comprising a sleeve having tapered distal and proximal ends respectively joined to said tip and said catheter tube;

said balloon assuming an annular cross-section when inflated and being generally symmetrical about an imaginary longitudinal axis; and said tapered distal and proximal ends joining said balloon to said tip and said catheter tube and aligning said stylet so that said stylet is substantially displaced from the longitudinal axis of said balloon to facilitate tight wrapping of the balloon about said stylet;

a luer connector;

a connector control member slidably mounted with said connector;

the proximal end of said stylet terminating in and being secured to said connector;

hollow flexible means coupling the proximal end of said catheter tube to said control member;

means for moving said control member in a first direction for stretching said balloon preparatory to percutaneous insertion or removal.

2. The balloon assembly of claim 1 wherein the apex of each of said tapered balloon ends are both offset from said balloon longitudinal imaginary axis.

3. The balloon assembly of claim 1 wherein said tapered balloon ends have one tapered portion and one straight portion substantially forming a right angle imaginary cone.

4. The balloon assembly of claim 1 wherein the balloon has an oval cross-section defined by a pair of flat surface portions joined to a pair of curved portions, the ends of said balloon being adjacent one of said curved portions and being joined to said tip and catheter tube so that the stylet engages the interior surface of one of said curved portions.

5. The balloon assembly of claim 4 wherein the remaining one of said curved portions is remote from said stylet.

6. The balloon assembly of claim 1 wherein the tapered ends of the balloon terminate in openings communicating with said tip and said catheter tube to place the stylet extending therethrough in close proximity with the interior surface along substantially the entire length of the balloon.

7. The balloon assembly of claim 1 wherein said stylet is secured to said tip.

8. The balloon assembly of claim 1 wherein said luer connector has a hollow interior for receiving said control member and is open at its opposing ends for respectively receiving said control member and for coupling to a pulsatile pressure source;

means for providing a gas-tight sliding seal between mid control member and the hollow interior of said luer connector.

9. The balloon assembly of claim 8 wherein said control member has a bore extending therethrough enabling the hollow interior of said luer connection to communicate with said catheter tube.

10. The balloon assembly of claim 8 wherein said luer connector is provided with a pair of diametrically opposed axially aligned slots each terminating in an enlarged opening having an offset portion;

said manually operable means having opposing ends each slidably mounted within one of said axially aligned slots and being releaseably locked within the offset portion of its associated enlarged opening.

11. The balloon assembly of claim 10 wherein said bias means comprises a helical spring positioned between one end of said control member and one interior surface of said luer connector for urging said control member in a first direction.

12. The balloon assembly of claim 10 wherein said guide slots extend to the open end of the luer connector receiving said control member;

the exterior periphery of the luer connector being provided with an annular groove spaced inwardly from the last-mentioned open end of the luer connector;

resilient metallic clip means mounted within said groove for preventing the pin from moving out of the open ends of said guide slots.

13. The balloon assembly of claim 8 wherein said luer connector is provided with a pair of diametrically opposed axially aligned guide slots;

said connector member being comprised of a cylindrical body having a bore extending therethrough;

a pin extending through said cylindrical body and being arranged perpendicular to the longitudinal axis of said cylindrical body, opposite ends of said pin extending through and slidable along an associated one of said guide slots.

14. The balloon assembly of claim 13 further comprising manual operating knobs arranged on the ends of said pin for manipulating said control member.

15. The balloon assembly of claim 13 further comprising a resilient O-ring arranged in an annular groove provided in the periphery of said control member forming an air-tight sliding seal between the interior of said luer connector and the periphery said control member.

16. The balloon assembly of claim 8 wherein said tip is comprised of a conductive member having a rounded tip portion and a body portion, said body portion extending into the distal end of said balloon and said tip extending beyond the distal end of said balloon;

the distal end of said stylet being electrically connected to said body portion;

electrical coupling means extending into the luer connector and having a first end electrically connected to the proximal end of said stylet and including a connector terminal external to the luer connector for coupling with a monitoring device.

17. The balloon assembly of claim 16 wherein the body portion of said conductive member is grooved to enhance the securement of the balloon distal end with said body portion.

18. The balloon assembly of claim 17 wherein said body portion of the balloon tip is of reduced diameter so that the distal end of the balloon is substantially flush with the rounded tip portion.

19. The balloon assembly of claim 1 wherein said balloon is wrapped about said stylet to facilitate insertion of the balloon into an insertion sheath which is adapted for insertion into a body vessel;

sheath splitter means arranged between proximal end of said catheter tube and said hollow flexible means and having cutter means for splitting the insertion sheath by pulling the sheath toward and past the cutter means of said sheath splitter means;

said sheath splitter means being hollow to enable the interior of said luer connector to communicate with the interior of said catheter tube.

20. The balloon assembly of claim 19 wherein the sheath splitter means is provided with a tubular connector end which is inserted into one end of a hollow flexible means;

the connector control member having a similar tubular end for insertion into the opposite end of said hollow flexible means.

21. The balloon assembly of claim 20 wherein said sheath splitter means and said hollow flexible means are hollow to enable to communicate with the interior of said luer connector.

22. The balloon assembly of claim 20 wherein said hollow flexible means comprises a flexible tubular plastic member;

the tubular ends of said control member and said sheath splitting means each being comprised of a plurality of truncated conical sections providing a plurality of annular vertices inserted into the tubular member for firmly gripping the flexible tubular member.

23. A balloon assembly adapted for percutaneous insertion and including an elongated tubular insertion sheath;

a balloon assembly adapted for facilitating insertion in a vessel comprising:

an elongated catheter tube;

an elongated balloon having a proximal end joined to one end of said catheter tube and having an opposite, distal end terminating in a tip;

a stylet having a distal end terminating in said tip and extending through said balloon and into said catheter tube;

said balloon comprising an inelastic sleeve having a tapered distal and proximal end respectively joined to said tip and said catheter tube;

said balloon assuming an annular cross-section when inflated and being generally symmetric about an imaginary longitudinal axis; and said tapered distal and proximal ends joining said balloon to said tip and said catheter tube and aligning said stylet so that said stylet is substantially displaced from the longitudinal axis of said balloon to facilitate tight wrapping of the balloon about said stylet;

a luer connector;

a connector control member slidably mounted within said connector;

the proximal end of said stylet terminating in and being secured to said connector;

hollow flexible means coupling the proximal end of said catheter tube to said control member;

means for moving said control member in a first direction for axially extending said balloon preparatory to percutaneous insertion or removal;

said balloon being wrapped about said stylet to facilitate insertion of the balloon into an insertion sheath which is adapted for insertion into a body vessel;

sheath splitter means arranged between the proximal end of said catheter tube and said flexible hollow means and having cutting means for splitting said sheath by pulling the sheath toward and past the cutter means of said sheath splitter means;

said sheath splitter means being hollow to enable the interior of said luer connector to communicate with the interior of said catheter tube;

the tip of the balloon being inserted into one end of said sheath.

24. The balloon assembly of claim 23 wherein said balloon is tightly wrapped in spiral fashion about said stylet;

a holder assembly for maintaining the balloon tightly wrapped preparatory to use.

25. The balloon assembly of claim 24 wherein said holder assembly has a bore for receiving said tightly wrapped balloon;

at least the surface of said bore having a low coefficient of sliding friction to facilitate removal of the balloon from the holder assembly by simply moving the catheter tube relative to the holder assembly to slide the balloon out of the holder assembly.

26. The balloon assembly of claim 24 wherein said holder assembly comprises two holder halves releaseably joined to one another by a cooperating tongue and groove arrangement.

27. The balloon assembly of claim 26 further comprising tape strips wrapped about and adhesively joined to said holder halves for securing said holder halves to one another.

28. A method for percutaneously inserting a balloon assembly comprised of sheath splitter means arranged between said catheter tube and said luer connector for splitting an elongated insertion sheath;

an elongated balloon having a proximal end joined to one end of said catheter tube and having an opposite, distal end terminating in a tip;

a stylet having a distal end terminating in said tip and extending through said balloon and into said catheter tube;

said balloon comprising a sleeve having tapered distal and proximal ends respectively joined to said tip and said catheter tube;

said balloon assuming an annular cross-section when inflated and being generally symmetric about an imaginary longitudinal axis; and said tapered distal and proximal ends joining said balloon to said tip and said catheter tube and aligning said stylet so that said stylet is substantially displaced from the longitudinal axis of said balloon to facilitate tight wrapping of the balloon about said stylet;

a luer connector;

a connector control member slidably mounted within said connector;

the proximal end of said stylet terminating in said connector;

the proximal end of said catheter tube being coupled to said control member;

means for moving said control member in a first direction for stretching said balloon preparatory to percutaneous insertion or removal;

said method comprising the steps of:

tightly wrapping the balloon about said stylet in spiral fashion;

retaining the balloon tightly wrapped by placing a holder assembler having a hollow interior about said balloon;

moving the connector control member in a first direction against said bias means for stretching the balloon;

placing a portion of a tubular insertion sheath into the body of patient;

inserting the tip of said balloon assembly into the exposed end of the insertion sheath;

pushing the balloon out of the holder assembly and into the sheath for proper location within the body;

removing the holder from the catheter tube;

pulling the insertion sheath out of the body and against said sheath splitter means for splitting the sheath;

moving the connector control member in a second direction for relieving the balloon of expansion preparatory to balloon inflation.

29. A method for preparing an intra-aortic balloon assembly for insertion into the body, said balloon assembly comprising a catheter tube and a balloon having a proximal end joined to the distal end of the catheter tube and having a distal end terminating in a tip; a stylet extending through said balloon and having a distal end terminating in said tip and a proximal end extending into the catheter tube; the balloon openings communicating with said tip and said catheter tube to hold the stylet is displaced from the longitudinal axis of the balloon, said method comprising the steps of:

evacuating the balloon assembly sufficient to collapse the balloon so that the balloon assumes a flat tape-like cross-section, defined by a pair of flat portions joined at their ends along folds, said stylet lying against the interior of one of said folds; and wrapping the balloon in a tight spiral about the stylet;

retaining the wrapped balloon in a holder;

extending the balloon and sliding the wrapped balloon out of one end of the holder and inserting the wrapped balloon into an insertion sheath as it emerges from the holder.

30. The method of claim 29 wherein the wrapping step further comprises the steps of wrapping the balloon at least several times about the stylet; releasing and reapplying the vacuum condition and thereafter wrapping the balloon several more turns about the stylet; and repeating the last-mentioned step until the balloon is completely wrapped about the stylet.

31. The method of claim 30 further comprising the step of retaining the wrapped balloon in a holder includes encasing the wrapped balloon between two holder halves.

32. The method of claim 31 further comprising the step of removing the holder from the balloon assembly after the balloon has completely emerged from the holder.

33. An intra-aortic balloon assembly comprising:

an elongated balloon having an annular cross-section generally concentric about a longitudinal axis; said balloon having distal and proximal ends terminating in openings which are offset from said longitudinal axis;

a catheter tube;

the proximal end of said balloon being joined to the distal end of said catheter tube;

the distal end of said balloon terminating in a tip;

a stylet having a distal end positioned in said tip and extending through said balloon distal and proximal ends and into said catheter tube;

said stylet extending generally along the centers of said distal and proximal ends and being offset from the longitudinal axis of said balloon;

a luer connector and means for coupling the connector to the proximal end of the catheter tube; the proximal end of the stylet extending through said coupling means and terminating in said connector; said coupling means including a connector control member slidably mounted in said connector for axially moving the catheter tube relative to the stylet to elongate said balloon.

34. The intra-aortic balloon assembly of claim 33 further comprising a locating indicia on the exterior of said catheter at a location sufficiently remote from said balloon to indicate the direction which the balloon extends away from said stylet to facilitate proper orientation of the balloon within the body.

35. An intra-aortic balloon assembly comprising a catheter tube;

an elongated balloon having an annular cross-section; the ends of said balloon terminating in openings;

the intermediate portion of said balloon being substantially uniform in diameter, said openings having diameters substantially smaller than the diameter of said balloon intermediate portion;

said openings being offset from said longitudinal axis;

the proximal end of said balloon being joined to the distal end of said catheter tube;

the distal opening of said balloon terminating in a tip;

a stylet extending through said catheter tube, said proximal opening, said balloon, said distal opening and terminating in said tip; and said balloon openings positioning said stylet offset from said longitudinal axis;

a luer connector coupled to the proximal end of the catheter tube;

the proximal end of the stylet extending into and terminating in said connector;

a connector control member slidably mounted in said connector and means for axially moving the catheter tube relative to the stylet.

36. The intra-aortic balloon assembly of claim 35 wherein said stylet is a hollow tubular member.

37. The intra-aortic balloon assembly of claim 36 wherein said tip has an opening communication with the hollow interior of said tubular stylet to permit insertion of a guide wire therethrough.

38. The intra-aortic balloon assembly of claim 35 further comprising a locating indicia on the exterior of a coupling joined to said catheter at a location sufficiently remote from said balloon to indicate the direction which the balloon extends away from said stylet to facilitate proper orientation of the balloon within the body.

39. The intra-aortic balloon of claim 35 wherein a sticky substance is deposited upon the exterior surface of said balloon to cause the balloon, when wrapped after application of said substance, to retain said wrapped condition; and said sticky substance being dissolvable in the bloodstream to release the balloon from the wrapped condition when the wrapped balloon is inserted into the body.

* * * * *

UNITED STATES PATENT AND TRADEMARK OFFICE
CERTIFICATE OF CORRECTION

PATENT NO. : 4,697,573
DATED : October 6, 1987
INVENTOR(S) : Peter Schiff

It is certified that error appears in the above-identified patent and that said Letters Patent are hereby corrected as shown below:

Col. 1, line 61, "the" should be --to--;

Col. 11, line 39, "served" should be --severed--.

Signed and Sealed this

Fifteenth Day of March, 1988

Attest:

DONALD J. QUIGG

Attesting Officer

Commissioner of Patents and Trademarks